(12) United States Patent
Jani

(10) Patent No.: US 12,697,436 B2
(45) Date of Patent: Aug. 4, 2026

(54) PATIENT CARE DEVICE CONFIGURED FOR AUTOMATIC ADJUSTMENT BASED ON IMAGE DATA

(71) Applicant: CareFusion 303, Inc., San Diego, CA (US)

(72) Inventor: Vinay Jani, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 25 days.

(21) Appl. No.: 18/975,657

(22) Filed: Dec. 10, 2024

(65) Prior Publication Data

US 2026/0158218 A1     Jun. 11, 2026

(51) Int. Cl.
*A61M 5/00*     (2006.01)
*A61B 8/08*     (2006.01)
*A61M 5/172*     (2006.01)

(52) U.S. Cl.
CPC ......... *A61M 5/1723* (2013.01); *A61B 8/0883* (2013.01); *A61M 5/007* (2013.01); *A61M 2205/3375* (2013.01); *A61M 2205/6009* (2013.01)

(58) Field of Classification Search
CPC ................ A61M 5/1723; A61M 5/007; A61M 2205/3375; A61M 2205/6009; A61B 8/0883
See application file for complete search history.

(56) References Cited

U.S. PATENT DOCUMENTS

2005/0182319 A1     8/2005   Glossop
2010/0331813 A1     12/2010  Robinson
2011/0070209 A1     3/2011   Franco
2024/0335215 A1     10/2024  Aliakbari et al.

FOREIGN PATENT DOCUMENTS

CN          118717267 A      10/2024

OTHER PUBLICATIONS

Kossaify, Antoine et al., "Stress Echocardiography: Concept and Criteria, Structure and Steps, Obstacles and Outcomes, Focused Update and Review", Cardiol Res. Apr. 2020; 11(2):89-96. doi: 10.14740/cr851. Epub Mar. 10, 2020. PMID: 32256915; PMCID: PMC7092766.

(Continued)

*Primary Examiner* — Michael T Rozanski
(74) *Attorney, Agent, or Firm* — MASCHOFF BRENNAN

(57)     ABSTRACT
The present disclosure regards an infusion system that includes an infusion device, an imaging device, and a processor. The processor is configured to pump a fluid, and the imaging device is configured to convert a received image signal into image data. The processor is configured to receive an identifier for the fluid and determine that the fluid is associated with an imaging-based infusion protocol based on the fluid identifier. The processor is also configured to detect whether the imaging device is connected to the imaging probe and, responsive to detecting that it is connected, operate the infusion device at a first operating speed. Additionally, the processor is configured to receive the image data from the imaging device and determine a second operating speed based on the image data. Further, the processor is configured to operate the infusion device at the second operating speed.

20 Claims, 4 Drawing Sheets

(56) References Cited

OTHER PUBLICATIONS

Krittanawong Chayakrit et al., "Deep Learning for Echocardiography: Introduction for Clinicians and Future Vision: State-of-the-Art Review", Life (Basel). Apr. 17, 2023;13(4):1029. doi: 10.3390/life13041029. PMID: 37109558; PMCID: PMC10145844.

Suzuki, Kenji, "Overview of deep learning in medical imaging", Radiol Phys Technol (2017) 10:257-273, DOI 10.1007/s12194-017-0406-5.

Crouch et al., "New Technology for the Treatment of Peripheral Arterial and Venous Occlusions: Ultrasound Accelerated Thrombolysis", Journal of Radiology Nursing, Elsevier Amsterdam, NL, vol. 27, No. 1, Feb. 27, 2008 (Feb. 27, 2008), pp. 14-21, XP022499139, ISSN: 1546-0843.

International Search Report and Written Opinion for Application No. PCT/US2025/056073, dated Mar. 11, 2026, 14 pages.

Kuo Wen-Chuan et al., "Optical Coherence Tomography Needle Probe in Neuraxial Block Application", IEEE Journal of Selected Topics in Quantum Electronics, IEEE, USA, vol. 27, No. 4, Dec. 9, 2020 (Dec. 9, 2020), pp. 1-6, XP011831289, ISSN: 1077-260X, DOI: 10.1109/JSTQE.2020.3042076 [retrieved on Jan. 11, 2021] p. 4, col. 2.

100

102

110

112

106A

104

106B

120

122

106A

114

106C

124

200

240

Information system server
242

Database
244

236

Device network
238

234

202

Funct'l Module
206

210

ROM
212

RAM
214

µP
216

Funct'l Module
207

...

ROM

RAM

µP

Control unit
204

CPU
218

224

Auxiliary interface
226

Disk
228

Network connection
220

User I/O
230

RAM
222

Data input device
232

Funct'l Module
208

...

ROM

RAM

µP

Funct'l Module
209

...

ROM

RAM

µP

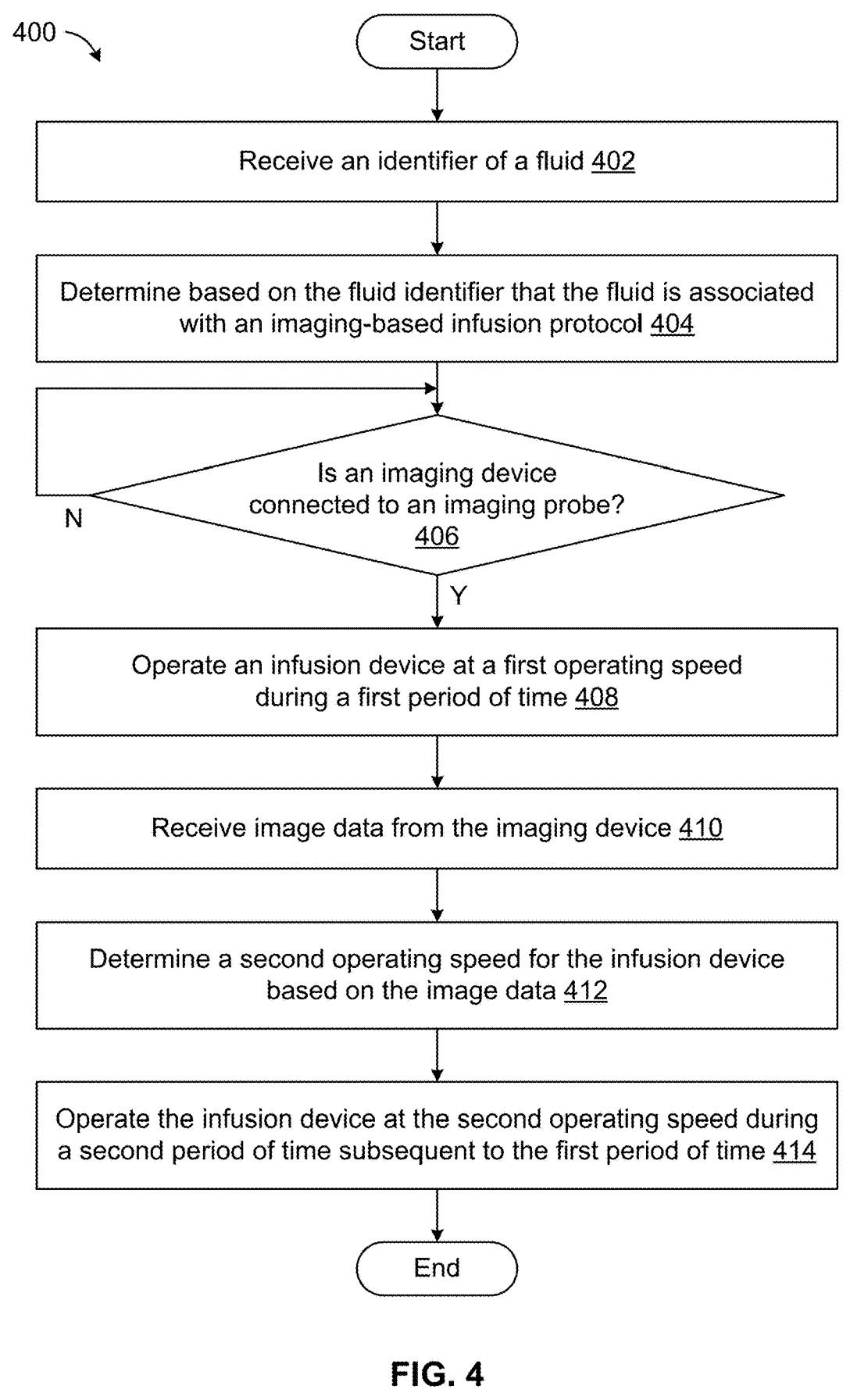

400

```
                        ┌──────────┐
                        │  Start   │
                        └──────────┘
                             │
                             ▼
        ┌────────────────────────────────────────────────┐
        │      Receive an identifier of a fluid 402       │
        └────────────────────────────────────────────────┘
                             │
                             ▼
        ┌────────────────────────────────────────────────┐
        │  Determine based on the fluid identifier that   │
        │  the fluid is associated with an imaging-based  │
        │            infusion protocol 404                │
        └────────────────────────────────────────────────┘
                             │
                             ▼
                 ◇─────────────────────◇
          N     Is an imaging device
        ◄───  connected to an imaging probe?
                        406
                 ◇─────────────────────◇
                             │ Y
                             ▼
        ┌────────────────────────────────────────────────┐
        │    Operate an infusion device at a first        │
        │  operating speed during a first period of       │
        │              time 408                           │
        └────────────────────────────────────────────────┘
                             │
                             ▼
        ┌────────────────────────────────────────────────┐
        │  Receive image data from the imaging device 410 │
        └────────────────────────────────────────────────┘
                             │
                             ▼
        ┌────────────────────────────────────────────────┐
        │  Determine a second operating speed for the     │
        │   infusion device based on the image data 412   │
        └────────────────────────────────────────────────┘
                             │
                             ▼
        ┌────────────────────────────────────────────────┐
        │ Operate the infusion device at the second       │
        │ operating speed during a second period of time  │
        │ subsequent to the first period of time 414      │
        └────────────────────────────────────────────────┘
                             │
                             ▼
                        ┌──────────┐
                        │   End    │
                        └──────────┘
```

FIG. 4

PATIENT CARE DEVICE CONFIGURED FOR AUTOMATIC ADJUSTMENT BASED ON IMAGE DATA

TECHNICAL FIELD

The present disclosure relates, generally, to medical devices and, more specifically, to the integration of infusion administration and medical imaging technologies.

BACKGROUND

Infusion administration and medical imaging technologies have made significant strides in the past few decades. Indeed, infusion devices and imaging devices alike are now prevalent in modern healthcare facilities throughout the world. Some procedures even employ these devices in tandem, such as dobutamine stress echocardiograms and ultrasound-guided central venous catheter placements.

Nonetheless, current imaging and infusion devices operate independently of one another, requiring manual interventions from a skilled technician. As a result, medical procedures that involve the simultaneous operation of infusion and imaging devices are complex and prone to human error. This is especially true for procedures that require medical imaging and corresponding infusion adjustments at multiple different stages throughout.

SUMMARY

The subject technology seeks to address the aforenoted problems by directly integrating infusion administration and medical imaging technologies. For instance, some implementations integrate these technologies by using image data to automatically adjust the operation of an infusion device. And some implementations integrate the technologies by generating imaging guidance based on the status of an ongoing infusion protocol. These and other implementations are discussed in more detail below.

Exemplary implementations of the subject technology include the following:

An Infusion System. The infusion system includes an infusion device configured to pump a fluid through an infusion line. The infusion system also includes an imaging device configured to receive an image signal from an imaging probe and convert the image signal into image data. Additionally, the infusion system includes a processor configured to receive an identifier of the fluid and determine based on the fluid identifier that the fluid is associated with an imaging-based infusion protocol. The processor is also configured to detect whether the imaging device is connected to the imaging probe and, responsive to detecting that the imaging device is connected to the imaging probe, operate the infusion device at a first operating speed during a first period of time. Additionally, the processor is configured to receive the image data from the imaging device and determine a second operating speed based on the image data. Further, the processor is configured to operate the infusion device at the second operating speed during a second period of time subsequent to the first period of time.

A Computer-Implemented Method. The computer-implemented method is for adjusting a patient care device based on image data. The method includes receiving an identifier of a fluid and determining based on the fluid identifier that the fluid is associated with an imaging-based infusion protocol. The method also includes detecting whether an imaging device is connected to an imaging probe, where the imaging device is configured to receive an image signal from the imaging probe and convert the image signal into image data. Additionally, the method includes, responsive to detecting that the imaging device is connected to the imaging probe, operating an infusion device at a first operating speed during a first period of time, where the infusion device is configured to pump the fluid through an infusion line. Further, the method includes receiving the image data from the imaging device and determining a second operating speed based on the image data. Moreover, the method includes operating the infusion device at the second operating speed during a second period of time subsequent to the first period of time.

A Non-Transitory, Computer-Readable Storage Medium. The storage medium includes instructions that when executed by a processor of an electronic device cause the processor to perform operations. The operations include receiving an identifier of a fluid and determining based on the fluid identifier that the fluid is associated with an imaging-based infusion protocol. The operations also include detecting whether an imaging device is connected to an imaging probe, where the imaging device is configured to receive an image signal from the imaging probe and convert the image signal into image data. Additionally, the operations include, responsive to detecting that the imaging device is connected to the imaging probe, operating an infusion device at a first operating speed during a first period of time, where the infusion device is configured to pump the fluid through an infusion line. Further, the operations include receiving the image data from the imaging device and determining a second operating speed based on the image data. Moreover, the operations include operating the infusion device at the second operating speed during a second period of time subsequent to the first period of time.

Based on the following Detailed Description, other configurations of the subject technology will be apparent to those skilled in the art. The Detailed Description describes various configurations of the subject technology, particularly with respect to illustrations thereof. Notwithstanding, the subject technology is capable of other and different configurations, and its several details are capable of modification in various other respects-all without departing from the scope of the subject technology. The Drawings and Detailed Description are therefore presented as illustrative in nature and should not be construed as restricting the present disclosure.

BRIEF DESCRIPTION OF THE DRAWINGS

For a better understanding of the present disclosure, reference should be made to the Detailed Description below in conjunction with the following drawings. Like reference numerals refer to corresponding parts throughout the figures and the description.

FIG. 4 depicts an example process for adjusting a patient care device based on image data, according to various aspects of the subject technology.

DETAILED DESCRIPTION

Reference will now be made to implementations, examples of which are illustrated in the accompanying drawings. In the following description, specific details are set forth in order to provide an understanding of the various described implementations. However, it will be apparent to one of ordinary skill in the art that the various described implementations may be practiced without one or more of these details. In other instances, well-known methods, procedures, components, circuits, and networks have not been described in detail so as not to unnecessarily obscure aspects of the implementations.

Figure 1:
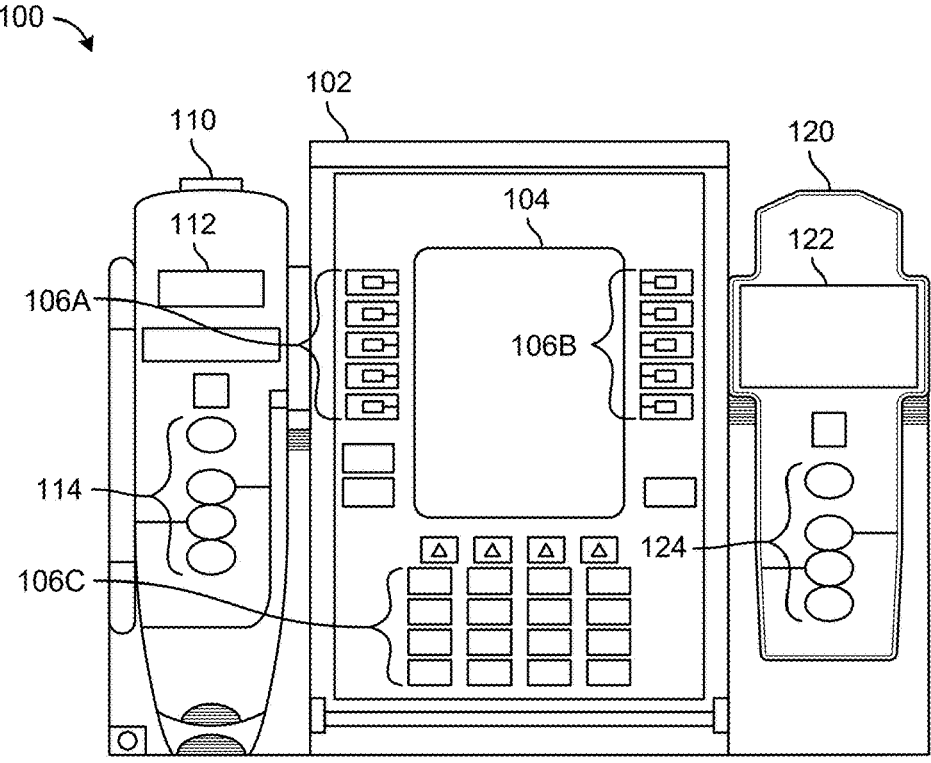
FIG. 1 illustrates an example patient care device that includes a control unit with a pumping module and an imaging module mounted thereon, according to various aspects of the subject technology.

FIG. 1 illustrates an example patient care device 100 that includes a control unit 102 with an infusion module 110 and an imaging module 120 mounted thereon, according to various aspects of the subject technology. The patient care device 100 represents one potential solution for integrating infusion and imaging technologies, with the control unit 102 acting as an intermediary between the two modules 110 and 120.

Figure 3:
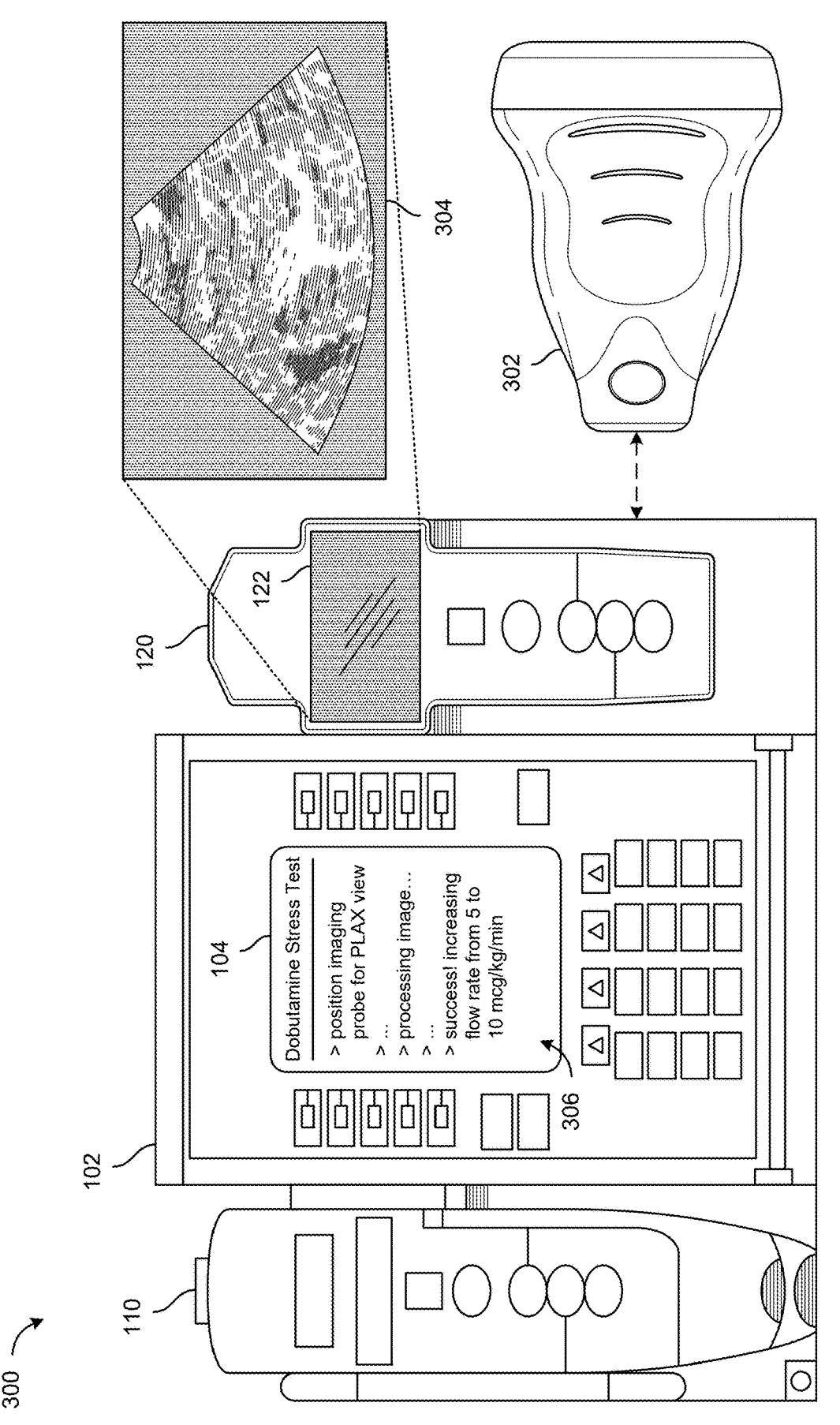
FIG. 3 illustrates an example infusion system that includes an imaging probe and a control unit mounted infusion and imaging modules, according to various aspects of the subject technology.

As discussed in more detail with respect to FIGS. 3 and 4, the control unit 102 can be configured to receive image data from the imaging module 120 and then use that data to adjust operation of the infusion module 110. For example, the control unit 102 can provide image data from the imaging module 120 to a machine learning model trained to determine conditions of a patient based on such data, received a condition from the model based on the image data, and index a lookup table by that condition to determine an operating speed adjustment for the infusion module 110. Additionally, the control unit 102 can be configured to guide a clinician in using an imaging probe connected to the imaging module 120 based on the status of the infusion module 110 or another parameter thereof. As an example, the control unit 102 can prompt the clinician to direct the imaging probe towards a particular area of a patient based on a total operating time of the infusion module 110 (e.g., to observe how a particular area of the body associated with the determined condition of the patient has been affected by the infusion).

In this manner, the patient care device 100 can significantly reduce the burden on a clinician tasked with performing a medical procedure that relies on both infusion and imaging technologies. The control unit 102 can aid, for instance, with a dobutamine stress test by (i) prompting a clinician to situate an imaging probe connected to the imaging module 120 to image a particular area of a patient's body and (ii) adjusting dobutamine flow at the infusion module 110 based on captured image data. As another example, the control unit 102 can use image data from the imaging module 120 to automatically ensure an infusion line connected to the infusion module 110 is properly situated before beginning an infusion protocol.

In the illustrated implementation, the infusion module 110 is a peristaltic pump that is in operative engagement with a respective administration set (not pictured). The administration set connects the infusion module 110 to a fluid supply (not pictured) at one end of the set and to a patient (not pictured) at the other end. The infusion module 110 is a flow control device configured to provide a fluid (e.g., a medication, a saline solution) to the patient. To accomplish this, the infusion module 110 is configured to act on the administration set to cause fluid to move therethrough. In some implementations, the infusion module 110 is a syringe pump or another type of pump capable of causing a fluid to flow through the administration set.

According to various implementations, the aforenoted control unit 102 is configured for programming the infusion module 110. In the illustrated implementation, the control unit 102 includes a display 104 and controls 106A-C (e.g., buttons) which allow a clinician to interface with the control unit 102. In some implementations, the display 104 is a touchscreen display. In such implementations, the control keys 106A-C may be omitted or reduced in number by providing alternative interactive elements via a graphical user interface presented at the display 104. In some implementations, the control keys 106A-C may select a corresponding option displayed in the display 104. Also, in addition to the display 104 and control keys 106A-C, the control unit 102 may also include a speaker configured to provide audible alerts.

In some implementations, the infusion module 110 includes its own display and/or controls. For example, in the depicted implementation, the infusion module 110 includes a display 112 (e.g., an LED display, a touchscreen display) which is located in plain view and may be used to visually communicate information regarding the infusion module 110. The display 112, for instance, can communicate alert indications or alarm messages. Additionally, control keys 114 of the module 110 allow for programming and controlling operations of the infusion module 110 as desired. In some implementations, the control keys 114 may be presented as interactive elements on the display 112. Like the control unit 102, the infusion module 110 may also include audio alert equipment (e.g., a speaker).

The other module 120 mounted to the control unit 102, the imaging module 120, is configured to receive an image signal from an imaging probe (e.g., an ultrasound probe) and convert the image signal into image data. The imaging module 120 then provides this image data to the control unit 102, which can use the data, for instance, to adjust the infusion module 110 or confirm catheter placement. Like the infusion module 110, the imaging module 120 includes a screen 122 (e.g., for displaying an ultrasound image based on the image data) and buttons 124 (e.g., for adjusting settings of the module 120 or a probe connected thereto).

In addition to the infusion and imaging modules 110 and 120, the patient care device 100 can also include various other modules, such as an additional infusion module (e.g., a peristaltic pump, a syringe pump), an additional imaging module (e.g., an ultrasound unit, an optical coherence tomography unit), a monitoring module (e.g., for patient vital signs), a medical dispensing module, a medication preparation module, and so on.

Figure 2:
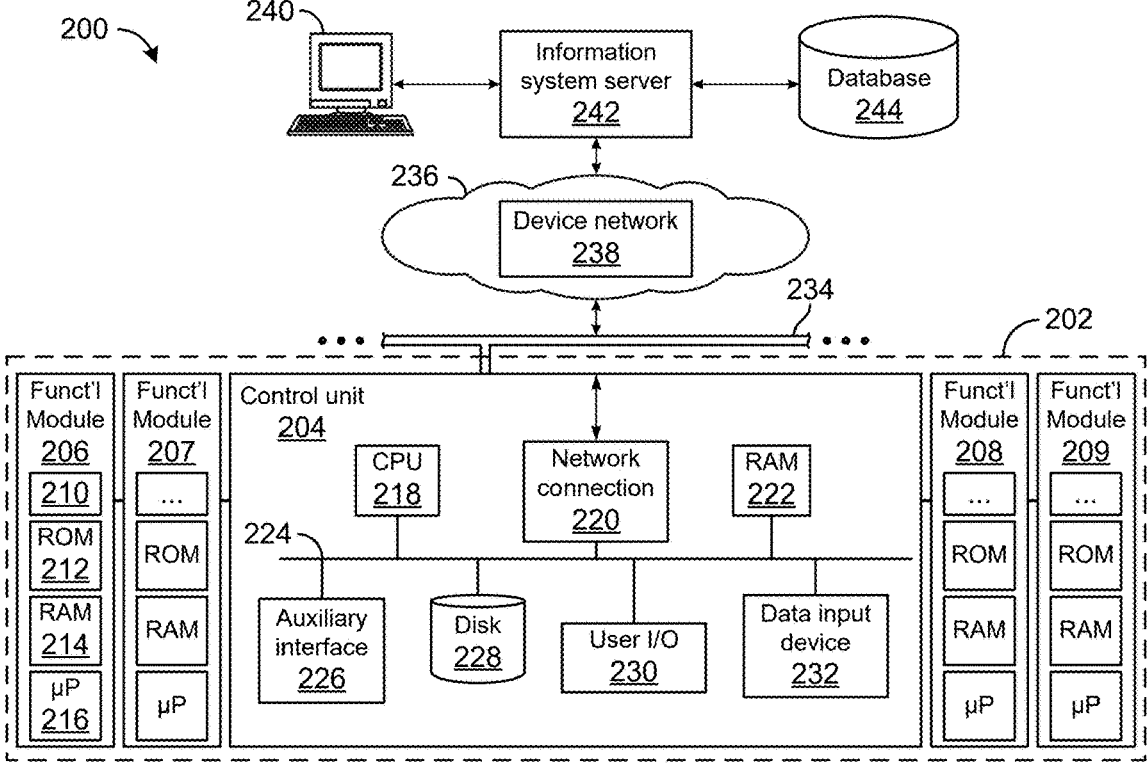
FIG. 2 illustrates an example patient care system of a healthcare organization, according to various aspects of the subject technology.

FIG. 2 depicts an example institutional patient care system 200 of a healthcare organization, according to various aspects of the subject technology. The system 200 includes a patient care device 202, such as the patient care device 100 of FIG. 1. The patient care device 202 is connected to an internal healthcare network 236. Each element of the patient care device 202 is connected to the healthcare network 236 via a transmission channel 234. The transmission channel 234 can be a wired or wireless transmission channel, such as an 802.11 wireless local area network (WLAN).

In some implementations, the internal healthcare network 236 also includes computer systems located in various departments throughout a hospital or healthcare center. For example, the internal healthcare network 236 optionally includes computer systems associated with an admissions department, a billing department, a biomedical engineering department, a clinical laboratory, a central supply department, one or more unit station computers, and/or a medical decision support system. In some implementations, the internal healthcare network 236 includes discrete subnetworks. In the depicted example, for instance, the internal healthcare network 236 includes a device network 238 by which the patient care device 202 and other devices can communicate in accordance with normal operations.

The institutional patient care system 200 may also incorporate a separate information system server 242 (e.g., a health information system server). Although the information system server 242 is shown as a separate server, the functions and programming of the information system server 242 may be incorporated into another computer. The institutional patient care system 200 may further include a device terminal 240 for connecting and communicating with information system server 242. The device terminal 240 may include personal computers, personal data assistants, or mobile devices (e.g., laptops, tablet computers, augmented reality devices, or smartphones) configured with software for communications with information system server 242 via the internal healthcare network 236.

The patient care device 202 includes a system for providing patient care, and it may include or incorporate infusion pumps (e.g., infusion module 110), imaging devices (e.g., imaging module 120), physiological monitors (e.g., a heart rate monitor, a blood pressure monitor, an electrocardiogram, an electroencephalogram, a pulse oximeter, and/or other monitors), therapy devices, and/or other drug delivery devices that may be utilized according to the teachings set forth herein.

In the depicted example, the patient care device 202 includes a control unit 204 (e.g., control unit 102), which is connected to one or more functional modules 206-209 (e.g., modules 110 and 120). Control unit 204 includes a central processing unit (CPU) 218 connected to a memory, for example, random access memory (RAM) 222, and one or more interface devices such as user interface device 230, a coded data input device 232, a network connection 220, and an auxiliary interface 226 for communicating with additional modules or devices. Control unit 204 also, although not necessarily, includes a main non-volatile storage unit 228, such as a hard disk drive or non-volatile flash memory, for storing software data. Additionally, control unit 204 may include one or more internal buses 224 for interconnecting the aforementioned elements.

In various implementations, user interface device 230 is a touch screen for displaying information to a user and allowing a user to input information by touching defined areas of the screen. Additionally, or in the alternative, user interface device 230 could include any means for displaying and inputting information, such as a monitor, a printer, a keyboard, softkeys, a mouse, a track ball, and/or a light pen.

Data input device 232 may be a bar code reader capable of scanning and interpreting data printed in bar coded format. Additionally, or in the alternative, data input device 232 can be any device for entering coded data into a computer, such as a device(s) for reading magnetic strips, radio-frequency identification (RFID) devices whereby digital data encoded in RFID tags or smart labels (defined below) are captured by the data input device 232 via radio waves, PCMCIA smart cards, radio frequency cards, memory sticks, CDs, DVDs, or any other analog or digital storage media. Other examples of the data input device 232 include a voice activation or recognition device or a portable personal data assistant (PDA). Depending upon the types of interface devices used, the user interface device 230 and the data input device 232 may be the same device. Although the data input device 232 is shown in FIG. 2 as being disposed within the control unit 204, the data input device 232 may be external to the control unit 204 (e.g., at the device terminal 240).

Auxiliary interface 226 may be an RS-232 communications interface, however any other means for communicating with a peripheral device (e.g., a printer, a patient monitor, an infusion pump, or another medical device) may be used without departing from the subject technology. Additionally, the data input device 232 may be a separate functional module (e.g., functional modules 206-207) configured to communicate with the control unit 204 or any other system on the network using suitable programming and communication protocols.

Network connection 220 may be a wired or wireless connection, such as by Ethernet, Wi-Fi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

The functional modules 206-209 are devices for providing care to a patient or for monitoring patient conditions. At least one of the functional modules 206-209 may be an infusion pump module (e.g., infusion module 110), such as an intravenous infusion pump for delivering medication or other fluid to a patient. Additionally, at least one of the functional modules 206-209 may be an imaging module (e.g., imaging module 120). For the purposes of this discussion, functional module 207 is an infusion pump module, and functional module 208 is an imaging module.

Each of the functional modules 206-209 may be any patient treatment or monitoring device including, but not limited to, an infusion pump (e.g., a syringe pump), a PCA pump, an epidural pump, an enteral pump, a blood pressure monitor, a pulse oximeter, an EKG monitor, an EEG monitor, a heart rate monitor, an intracranial pressure monitor, a medical imaging interface (e.g., imaging module 120), or the like. Additionally, the functional modules 206-209 may include a printer, a scanner, a bar code reader, a near-field communication reader, an RFID reader, or any other peripheral input, output or input/output device.

Each functional module 206-209 communicates directly or indirectly with the control unit 204, providing overall monitoring and control of the patient care device 202. Additionally, the functional modules 206-209 may be connected physically and electronically in serial fashion to one or both ends of control unit 204 as shown in FIG. 2. However, it is recognized that there are other means for connecting the functional modules 206-209 with the control unit 204 that may be utilized without departing from the subject technology. It is also appreciated that devices such as pumps or patient monitoring devices that provide sufficient programmability and connectivity may be capable of operating as stand-alone devices and may communicate directly with the internal healthcare network 236 without being connected through the control unit 204 or a separate inter-face unit. As described above, additional medical devices or peripheral devices may be connected to the patient care device 202 through one or more auxiliary interfaces 226.

Each of the functional modules 206-209 may include various internal components such as those illustrated in FIG. 2. For example, the first functional module includes a microprocessor 216, a volatile memory 214, a nonvolatile memory 212, and other module-specific components 210. It should be noted that while four functional modules are shown in FIG. 2, any number of devices may be connected directly or indirectly to the control unit 204. The number and type of functional modules described herein are intended to be illustrative, and they in no way limit the scope of the subject technology. The module-specific components 210 include any components necessary for operation of a par-ticular module, such as a pumping mechanism for the functional module 206.

Additionally, while each of the functional modules 206-209 may be capable of a least some level of independent operation, the control unit 204 monitors and controls overall operation of the patient care device 202. For example, as will be described in more detail below, the control unit 204 provides programming instructions to the functional mod-ules 206-209 and monitors the status of each of the func-tional modules 206-209.

FIG. 3 illustrates an example infusion system 300 that includes an imaging probe 302 and a control unit 102 with mounted infusion and imaging modules 110 and 120, according to various aspects of the subject technology. This system 300 is configured to assist users with procedures that rely on medical imaging and infusion administration.

After a user selects a particular procedure, the control unit 102 can then display steps 306 for the selected procedure (e.g., via display 104). If the control unit 102 determines that the selected procedure has imaging and/or infusion ele-ments, the control unit 102 can also instruct the user to connect the corresponding modules 110 and/or 120 if the are not already connected. Likewise, the control unit 102 can also detect whether the imaging probe 302 is connected to the imaging module 120 and remind the user to connect the probe 302 if necessary.

In the illustrated example, the control unit 102 has received a request for assistance with a dobutamine stress echocardiogram, also referred to herein as a dobutamine stress test. This is one many procedures involving imaging and infusion that the system 300 can assist with. In accor-dance with this request, the control unit 102 displays example steps 306 for a dobutamine stress test.

The first of these example steps 306 instructs the user to position the imaging probe 302 to image a particular area of the patient's body (e.g., for a parasternal long axis (PLAX) view). The imaging probe 302 is configured to capture an image signal and then transmit the captured signal to the imaging module 120. And the imaging module 120 is configured to convert the image signal from the imaging probe 302 into image data, which the module 120 then displays via its display 122.

The imaging module 120 also forwards the image data to the control unit 102, which can determine based on the image data whether one or more criteria for the selected procedure are satisfied. In the illustrated example, the sec-ond of the steps 306 displayed at the control unit 102 indicates that the control unit 102 is processing the image data. For example, processing the image data may involve the application of computer vision or other image analysis algorithms to determine, for instance, whether the user correctly positioned the imaging probe 302 for the imaging the requested area of the patient's body (e.g., based on detecting in the image data atrial anatomy consistent with a PLAX view, such as an interventricular septum, ascending aorta, and the like). In some implementations, processing the data includes measuring one or more distances depicted in the image data (e.g., a width of a valve of the patient's heart) and then determining based on the one or more measure-ments, whether the patient is ready for an increased dose of a medication (e.g., dobutamine). The measurement may be performed by a processor configured to analyze features shown in the image using image recognition or machine learning techniques such as those described in U.S. Patent App. Pub. No. 2005/0182319 or Suzuki, "Overview of Deep Learning in Medical Imaging," Raidol. Phys. Technol. (2017) 10:257-273, each of which are hereby incorporated by reference.

The third of the example steps 306 indicates that the control unit 102 has successfully processed the image data and determined that the flow rate of dobutamine should be increased from five to ten micrograms per kilograms per minute. This determination can happen automatically with-out requiring the clinician to manually analyze the image data; however, in some implementations, the control unit 102 will confirm its findings regarding the image data before automatically adjusting the operating speed of the infusion module 110.

Thereafter, the control unit 102 can provide further steps 306 to the user via the display 104 based, for instance, on the status of the infusion module 110 and the infusion protocol performed thereby. As an example, after the infusion module 110 confirms with the control unit 102 that it has pumped a predetermined amount of dobutamine or pumped for a predetermined amount of time, the control unit 102 may display a step 306 instructing the user to position the imaging probe 302 to capture image data for another area of the patient's body (e.g., for an apical four chambers, A4C, view; an apical two chambers, A2C, view; a parasternal short-axis, SAX, view). Based on additional image data corresponding to the requested view, the control unit 102 can then adjust the infusion module 110 again. After said adjust-ment, the control unit 102 can display further steps 306 and acquire further image data, and so on until the selected procedure is complete.

Another example of a procedure the system 300 can assist with is an ultrasound-guided central venous catheter place-ment. In such implementations, the control unit 102 can display steps 306 instructing the user to position the imaging probe 302 at a vascular access site of a catheter (e.g., at a wrist or inner elbow of the patient). After receiving image data from the imaging module 120, the control unit 102 can then determine based on the imaging data whether the catheter was properly inserted at the vascular access site or whether the site is appropriate for insertion. This determi-nation may involve, for instance, identifying a vein in the image data, identifying a catheter in the image data, and then confirming whether the catheter is correctly placed in the vein. The confirmation may be automated using machine learning or other automated image analysis. In some imple-mentations, the confirmation may include presenting an image along with a control element (e.g., button) that, when activated, indicates confirmation of placement shown in the image.

Yet another example of procedures the system 300 can assist with is imaging protocols involving a contrast die infusion and computed tomography (CT) or machine-reso-nance imaging (MRI). These protocols are especially sensitive due to the need for specific imaging of physiologic structures (e.g., by attenuating other features). However, the contrast enhancement needed for these structures is complex because it depends on timing and patient-related factors. The system 300 can be used to alleviate some of this complexity by automating the programming of contrast agent infusion, correcting for patient specific parameters, and correcting for imaging-specific needs (e.g., breath holds).

In such implementations, the user can select a CT/MRI contrast protocol from a list of protocols displayed at the control unit 102. The user can also select a specific physiology of interest (e.g., left-ventricular imaging). Thereafter, the control unit 102 will acquire data regarding the patient's blood pressure or heart rate, as well as data regarding the patient's pathophysiology (e.g., heart failure). From there, the control unit 102 will auto-populate an infusion program and generate steps 306 for the requested procedure (e.g., based on a transfer program).

In CT/MRI implementations, the control unit 102 and/or the imaging module 120 can automatically enhance image data to account for various patient-related factors, such as weight, height, cardiac output, age, sex, renal function, venous access, breath holds, and/or comorbidities. Additionally, the control unit 102 can also process the image data to automatically determine whether to adjust the infusion module 110, for instance, by changing a flow rate of the contrast agent, or adjusting an iodine concentration, volume, bolus shape, vascular access, velocity, and/or injection protocol thereof. These and other adjustments are based on calculations performed by the control unit 102 based on the image data—for example, if the control unit 102 determines that the flow rate of the contrast agent should be increased to improve imaging, the control unit 102 can cause such an adjustment at the infusion module 110.

As one specific example, after administering the contrast agent at a first rate for a predetermined amount of time, the image may be processed to determine an amount of contrast agent in the captured image. If there is no contrast agent or insufficient contrast agent in the image, the control unit 102 may increase the rate of administration of the contrast agent for a period of time to improve imaging. If there is sufficient contrast agent detected, the control unit 102 may pause administration of further contrast agent or slow the flow rate thereof. As images are acquired over time, the administration of contrast agent may be adjusted to maintain a consistent or desired amount of contrast (e.g., in subsequently captured images).

As another example, different contrast agents may be administered in a sequence using two different infusion modules (e.g., infusion module 110 and another such infusion module). In this example, as the set of image data is analyzed based on a first contrast agent administered by the first of the infusion modules, if the image analysis indicates the first contrast agent is providing sufficient clarity, the control unit 102 may slow or stop the first infusion module administering the first contrast agent and cause the second of the two infusion modules to administer a second contrast agent. For instance, the control unit 102 may slow the flow rate of the first infusion module (e.g., slow flow rate by 50% or 85%) after detecting the first contrast agent in the image data and determining that a difference between a brightness of the contrast agent and a brightness of the surrounding area satisfies a clarity threshold (e.g., requiring at least a 25% difference).

According to various CT/MRI implementations, the control unit 102 is also configured to automatically order one or more CT/MRI scans after receiving a selected procedure and determining the selected procedure requires one or more CT/MRI scans. For instance, the control unit 102 may determine the selected procedure requires a CT/MRI scan based on a type of the selected procedure and querying a lookup table using the procedure type. Additionally, in some implementations, the control unit 102 can accept diagnostic parameters from an analyzed image (or analyze the image using deep learning) and adjust the infusion module 110 accordingly (e.g., adjust contrast volume, flow rate, etc.).

Further, it is noted that, in implementations specifically involving MRI, shielding may be necessary to prevent unintended interference between the MRI imaging device and the control unit 102 and modules 110 and 120 attached thereto. Accordingly, in some implementations, the infusion system 300 includes shielding surrounding the control unit 102, the infusion module 110, and the imaging module 120.

FIG. 4 depicts an example process 400 for adjusting a patient care device (e.g., control unit 102, infusion module 110) based on image data (e.g., from imaging module 120), according to various aspects of the subject technology. For explanatory purposes, the present disclosure describes the blocks of the example process 400 with reference to FIGS. 1 through 3 and the components described therein, including the control unit 102, infusion module 110, and imaging module 120 of FIGS. 1 and 3. One or more of the blocks of the process 400 may be implemented, for instance, by one or more processors of these devices, such as a processor (e.g., CPU 218) of the control unit 102, a processor (e.g., microprocessor 216) of a module connected to the control unit 102 (e.g., infusion module 110, imaging module 120), or a processor of another device (e.g., device terminal 240) connected to any of these devices.

In some implementations, one or more of the blocks may be implemented based on one or more machine-learning algorithms. In some implementations, one or more of the blocks may be implemented apart from other blocks, and by one or more different processors or devices. Further, for explanatory purposes, the blocks of the process 400 are described as occurring in serial, or linearly. However, multiple blocks of the process 400 may occur in parallel. Additionally, the blocks of the process 400 need not be performed in the order shown and one or more of the blocks of the process 400 need not be performed.

In the depicted example, the processor receives an identifier of a fluid (402) and determines, based on the fluid identifier, that the fluid is associated with an imaging-based infusion protocol (404). In some implementations, this determination involves providing the fluid identifier to a lookup table with information regarding which fluid types are associated with imaging-based infusion protocols, such as dobutamine or contrast fluids. Alternatively, or additionally, the processor can receive a procedure request and determine that the requested procedure involves an imaging-based infusion protocol (e.g., using a lookup table).

For purposes of this disclosure, an "imaging-based infusion protocol" is an infusion protocol that requires or at least relies on imaging data, such as the dobutamine stress test discussed for FIG. 3. Other imaging-based infusion protocols include ultrasound-guided central venous catheter placements and CT/MRI contrast protocols.

The processor also determines whether an imaging device (e.g., imaging module 120) is connected to an imaging probe (e.g., imaging probe 302) (406). If the imaging device is not connected to the imaging probe, then the processor delays until it determines that the imaging device and imaging probe are connected. Thereafter, the processor operates an infusion device (e.g., infusion module 110) at a first operating speed during a first period of time (408).

Additionally, the processor receives image data from the imaging device (410). This image data is converted by the imaging device from an image signal received from the imaging probe, as discussed for FIG. 3. In some implementations, the image data includes an ultrasound image, an optical coherence tomography (OCT) image, a CT image, or an MRI image.

Based on the image data, the processor determines a second operating speed for the infusion device (412). For instance, this determination may involve analyzing the image (e.g., using machine learning or deep learning) to extract one or more measurements of an organ, valve, or other organic material depicted in the image. Based on said measurements, the processor may then determine whether the one or more measurements satisfy corresponding predetermined thresholds. The determination can involve additional or other steps, as those skilled in the art will appreciate. After the second operating speed is determined, the processor then operates the infusion device at the second operating speed during a second period of time subsequent to the first period of time (414).

Before executing the process 400, the processor can require preliminary imaging, for instance, to determine whether the imaging probe is properly calibrated or is properly inserted into the patient. Accordingly, in some implementations, the processor is further configured to, responsive to detecting that the imaging device is connected to the imaging probe but prior to operating the infusion device at the first operating speed during the first period of time, prompt a user to image a patient with the imaging probe. The patient is an intended recipient of the fluid to be pumped through the infusion line by the infusion device. After receiving preliminary image data from the imaging device, the processor can then determine whether the preliminary image data satisfies a predetermined criterion (e.g., a calibration criterion, an insertion criterion). If the predetermined criterion is not satisfied, the processor can delay operating the infusion device at the first operating speed during the first period of time until after determining that the preliminary image data satisfies the predetermined criterion.

The processor can also be configured to assist a user by providing steps for guiding the user in using the imaging probe. In some implementations, the processor is further configured to, after operating the infusion device at the first operating speed during the first period of time but prior to receiving the image data from the imaging device, prompt a user to situate the imaging probe to image a particular area of a patient's body (e.g., for a PLAX view, an A4C view, an A2C view, a SAX view). The patient is an intended recipient of the fluid to be pumped through the infusion line by the infusion device. After receiving the image data but prior to determining the second operating speed based on the image data, the processor can determine whether the image data depicts the particular area of the patient's body. If it does not, the processor can delay determining the second operating speed based on the image data until after determining that the image data depicts the particular area of the patient's body.

Additionally, the processor can provide additional guidance for the user. According to various implementations, the processor is further configured to, after operating the infusion device at the second operating speed during the second period of time but prior to receiving additional image data from the imaging device, prompt a user to situate the imaging probe to image another particular area of the patient's body. After receiving the additional image data from the imaging device, the processor can then confirm that the additional image data depicts the other particular area of the patient's body. If the additional image data depicts the other particular area of the patient's body, then the processor can determine a third operating speed based on the additional image data and operate the infusion device at the third operating speed during a third period of time subsequent to the first and second periods of time.

Further, the processor can use machine- or deep-learning to assist with determining the second operating speed based on the image data. According to various implementations, the processor determining the second operating speed based on the image data includes providing the image data to a machine-learning (or deep-learning) model trained using training image data and corresponding training operating speed adjustment data, and then receiving the second operating speed from the machine-learning (or deep-learning) model.

As discussed with respect to FIG. 3, the processor can execute the process 400 in furtherance of a dobutamine stress test. For example, after receiving a request for a dobutamine stress test (e.g., included in an order or an automated programming request), the processor can cause the infusion module to pump dobutamine at a first flow rate (e.g., 5 mcg/kg/min) for a first period of time (e.g., 3 mins). The processor can also prompt the user to position the imaging probe to image a particular area of a patient's body (e.g., for a PLAX view, an A4C view, an A2C view, a SAX view), where the patient is an intended recipient of the fluid to be pumped through the infusion line by the infusion device. (If the processor determines the imaging probe is not connected, it can request that the user connect it to the imaging module.) After the first period of time and after receiving imaging data of the particular area of the patient's body (and, optionally, confirming that the imaging data corresponds to the requested area), the processor can then cause the infusion module to pump the dobutamine at a second flow rate (e.g., 10 mcg/kg/min) for a second period of time. This can continue for any number of flow rate adjustments and corresponding areas (or views)—as dictated by the parameters of the dobutamine stress test or another requested procedure.

In implementations involving dobutamine stress tests, the processor can cause the infusion device to pump the dobutamine at particular flow rates. For instance, the infusion device operating at the first operating speed can causes the fluid to flow at a first flow rate of five micrograms per kilogram per minute, and determining the second operating speed based on the image data can include determining the infusion device should cause the fluid to flow at a greater flow rate of ten or more micrograms per kilogram per minute based on the image data satisfying a predetermined characteristic. This predetermined characteristic can include a dimension of a valve depicted in the image data satisfying (e.g., exceeding) a particular threshold.

The imaging probe can be wired or wireless, and it can also include various imaging technologies. In many implementations, the imaging probe is an ultrasound imaging probe. However, according to various implementations, the imaging probe is an OCT probe, a CT probe, or an MRI probe.

In some implementations, the processor receives a selected therapy (e.g., a dobutamine stress test) and then determines or retrieves default steps for the selected therapy. For instance, the processor can retrieve said steps from a lookup table using an identifier of the selected therapy (e.g., indicating a type of the therapy). Alternatively, or additionally, the selected therapy can be received as part of an automated programming request including the default steps therefor. After receiving the selected therapy, if the processor determines that the therapy can incorporate image data, the processor can then prompt the user to connect the imaging probe to the imaging module if it is not already connected thereto. Image data (e.g., ultrasound data) collected by the imaging probe can be sent to the processor via the imaging module. The image data can also be displayed at the imaging module and/or the controller along with real-time information from the infusion module (e.g., regarding flow rate, volume). Additionally, the image data can be sent to a picture archiving and communication system (PACS), which can be integrated into information technology for a given healthcare organization (e.g., hospital IT).

Figure 5:
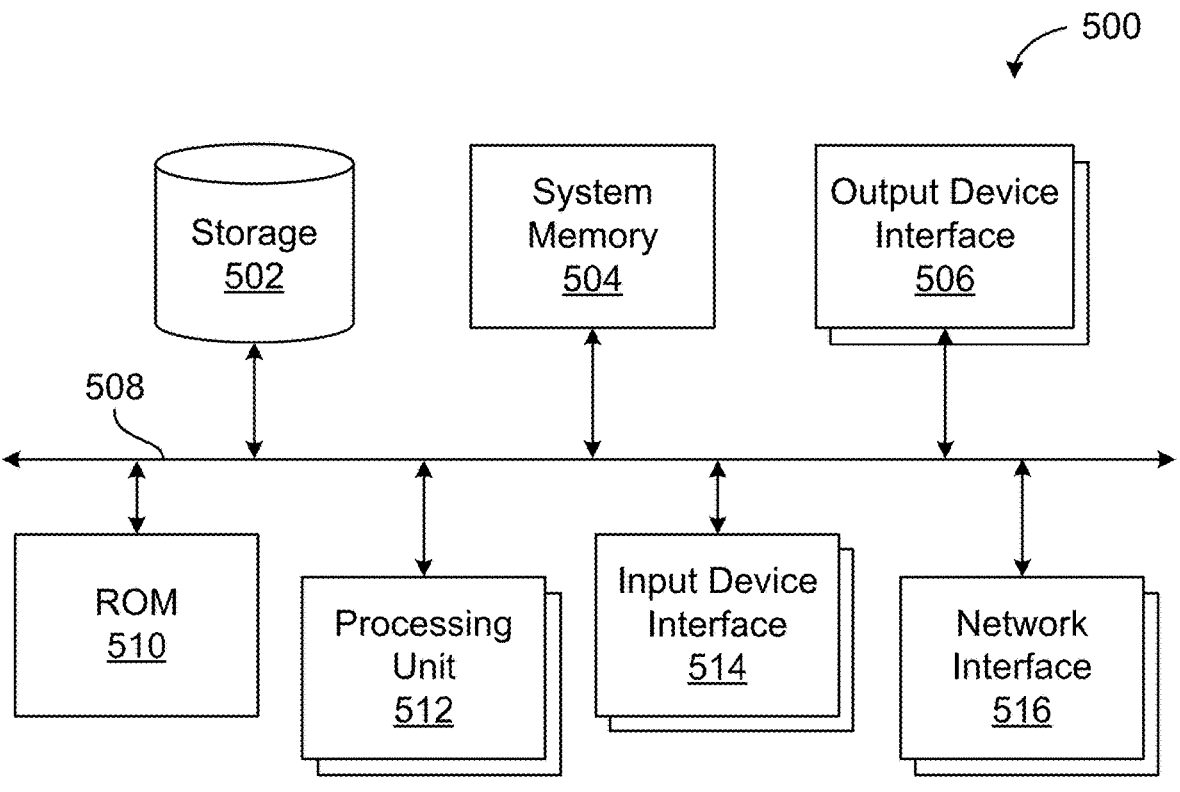
FIG. 5 illustrates an example electronic system for adjusting a patient care device based on image data, according to various aspects of the subject technology.

FIG. 5 illustrates an example electronic system 500 for cleaning medical devices, according to various aspects of the subject technology. The example electronic system 500 may be implemented by a computing device for execution of software associated with portions or steps of processes 400 and/or 450 of FIGS. 4A and 4B, or components provided by FIGS. 1 through 3. In this regard, the electronic system 500 may include a control unit 102, an infusion module 110, and an imaging module 120.

The electronic system 500 may also include a specifically-configured personal computer or a mobile device for infusion such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Additionally, the electronic system 500 may include various types of computer-readable media and interfaces for various other types of computer-readable media. In the depicted example, electronic system 500 includes a bus 508, one or more processing units 512, a system memory 504, a read-only memory (ROM) 510, a permanent storage device 502, one or more input device interfaces 514, one or more output device interfaces 506, and one or more network interfaces 516. In some implementations, electronic system 500 may include or be integrated with other computing devices or circuitry for operation of the various components and methods previously described.

Bus 508 collectively represents system, peripheral, and chipset buses that communicatively connect the numerous internal devices of electronic system 500. For instance, the bus 508 communicatively connects the one or more processing units 512 with the ROM 510, the system memory 504, and permanent storage device 502. From these various memory units, the one or more processing units 512 retrieve instructions to execute and data to process in order to execute the processes of the subject disclosure. The processing unit(s) 512 can be a single processor or a multi-core processor in different implementations.

The ROM 510 stores static data and instructions that are needed by the processing unit(s) 512 and other modules of the electronic system. On the other hand, the permanent storage device 502 is a read-and-write memory device. This device 502 is a non-volatile memory unit that stores instructions and data even when the electronic system 500 is powered off. Some implementations of the subject disclosure use a mass-storage device (e.g., magnetic storage, an optical disk and a corresponding disk drive) as the permanent storage device 502. Other implementations use a removable storage device (e.g., a flash drive, a floppy disk and a corresponding disk drive) as permanent storage device 502.

Like the permanent storage device 502, the system memory 504 is a read-and-write memory device. However, unlike storage device 502, the system memory 504 is a volatile read-and-write memory, such as random-access memory (RAM). The system memory 504 stores some of the instructions and data that the processor needs at runtime. In some implementations, the processes of the subject disclosure are stored in the system memory 504, the permanent storage device 502, and/or the ROM 510. From these various memory units, the processing unit(s) 512 retrieves instructions to execute and data to process, in order to execute the processes of some implementations.

The bus 508 also connects to one or more input device interfaces 514 and output device interfaces 506. The input device interface(s) 514 enables the user to communicate information and select commands to the electronic system. Input devices used with the input device interface(s) 514 include, for example, alphanumeric keyboards and pointing devices (also called "cursor control devices"). The output device interface(s) 506 enables, for example, the display of images generated by the electronic system 500. Output devices used with the output device interface(s) 506 include, for example, printers and display devices, such as cathode ray tubes (CRT) or liquid crystal displays (LCD). Some implementations include devices (e.g., touchscreens) that function as both input and output devices.

Furthermore, the bus 508 also couples the electronic system 500 to a network (not shown) through the network interface(s) 516. The network interface(s) 516 may include, for example, a wireless access point (e.g., Bluetooth or Wi-Fi) or radio circuitry for connecting to a wireless access point. The network interface(s) 516 may also include hardware (e.g., ethernet hardware) for connecting the computer to a part of a network of computers such as a local area network (LAN), a wide area network (WAN), wireless LAN, an intranet, or a network of networks, such as the Internet. Components of the electronic system 500 can be used in conjunction with the subject disclosure when specifically configured with one of more of the features described.

The functions described above can be implemented in computer software, firmware, or hardware. The techniques can be implemented using one or more computer program products. Programmable processors and computers can be included in or packaged as mobile devices. The processes and logic flows can be performed by one or more programmable processors and by programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field-programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices specifically configured with one or more of the features described above. These terms exclude people or groups of people. For the purposes of the specification, the terms display or displaying means displaying on an electronic device. As used in this specification and any claims of this application, the terms "computer-readable medium" and "computer-readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well. For example, feedback provided to the user can be any form of sensory feedback (e.g., visual feedback, auditory feedback, tactile feedback), and input from the user can be received in forms such as acoustic, speech, gesture, or tactile input. In addition, a computer can interact with a user by sending documents to and receiving documents from a device that is used by the user (e.g., by sending web pages to a web browser on a user's client device in response to requests received from the web browser).

Implementations of the subject matter described in this specification can be implemented in a specifically configured computing system that includes a back end component (e.g., a data server), or that includes a specifically configured middleware component (e.g., an application server), or that includes a specifically configured front end component (e.g., a client computer having a graphical user interface or a Web browser through which a user can interact with an implementation of the subject matter described in this specification), or any combination of one or more such back end, middleware, or front end components. The components of the system can be interconnected by one or more forms or mediums of digital data communication, such as a communication network. Examples of communication networks include a LAN and a WAN, an inter-network (e.g., Internet), and peer-to-peer networks (e.g., ad hoc peer-to-peer networks).

The computing system can include specifically configured clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Illustrative Clauses. For further reference, example aspects of the present disclosure are included below as numbered clauses. These clauses are provided for illustrative purposes and are not intended to limit the subject technology.

Clause 1. An infusion system comprising: an infusion device configured to pump a fluid through an infusion line; an imaging device configured to receive an image signal from an imaging probe and convert the image signal into image data; and a processor configured to: receive an identifier of the fluid; determine based on the fluid identifier that the fluid is associated with an imaging-based infusion protocol; detect whether the imaging device is connected to the imaging probe; responsive to detecting that the imaging device is connected to the imaging probe, operate the infusion device at a first operating speed during a first period of time; receive the image data from the imaging device; determine a second operating speed based on the image data; and operate the infusion device at the second operating speed during a second period of time subsequent to the first period of time.

Clause 2. The infusion system of Clause 1, wherein the processor is further configured to, responsive to detecting that the imaging device is connected to the imaging probe but prior to operating the infusion device at the first operating speed during the first period of time: prompt a user to image a patient with the imaging probe, wherein the patient is an intended recipient of the fluid to be pumped through the infusion line by the infusion device; receive preliminary image data from the imaging device, wherein the preliminary image data is converted by the imaging device from a preliminary image signal received from the imaging probe; determine whether the preliminary image data satisfies a predetermined criterion; and delay operating the infusion device at the first operating speed during the first period of time until after determining that the preliminary image data satisfies the predetermined criterion.

Clause 3. The infusion system of Clause 2, wherein: the infusion line is fluidically coupled to the patient via a catheter; and determining whether the preliminary image data satisfies the predetermined criterion comprises determining whether the preliminary image data indicates that the catheter is properly inserted into the patient.

Clause 4. The infusion system of any one of Clauses 1 through 3, wherein the processor is further configured to: after operating the infusion device at the first operating speed during the first period of time but prior to receiving the image data from the imaging device, prompt a user to situate the imaging probe to image a particular area of a patient's body, wherein the patient is an intended recipient of the fluid to be pumped through the infusion line by the infusion device; responsive to receiving the image data but prior to determining the second operating speed based on the image data, determine whether the image data depicts the particular area of the patient's body; and delay determining the second operating speed based on the image data until after determining that the image data depicts the particular area of the patient's body.

Clause 5. The infusion system of Clause 4, wherein the processor is further configured to: after operating the infusion device at the second operating speed during the second period of time but prior to receiving additional image data from the imaging device, prompt the user to situate the imaging probe to image another particular area of the patient's body; receive the additional image data from the imaging device, wherein the additional image data is converted by the imaging device from an additional image signal received from the imaging probe; confirm that the additional image data depicts the other particular area of the patient's body; responsive to confirming that the additional data depicts the other particular area of the patient's body, determine a third operating speed based on the additional image data; and operate the infusion device at the third operating speed during a third period of time subsequent to the first and second periods of time.

Clause 6. The infusion system of any one of Clauses 1 through 5, wherein determining the second operating speed based on the image data comprises: providing the image data to a machine-learning model trained using training image data and corresponding training operating speed adjustment data; and receiving the second operating speed from the machine-learning model.

Clause 7. The infusion system of any one of Clauses 1 through 6, wherein: the processor is further configured to: after operating the infusion device at the first operating speed during the first period of time but prior to receiving the image data from the imaging device, prompt a user situate the imaging device to obtain the image data by imaging a particular area of a patient's body, wherein the patient is an intended recipient of the fluid to be pumped through the infusion line by the infusion device; and responsive to receiving the image data but prior to determining the second operating speed based on the image data, confirm that the image data depicts the particular area of the patient's body.

Clause 8. The infusion system of Clause 7, wherein the processor is further configured to: display, on a display screen, the image data in (i) a parasternal long axis view, (ii) an apical four chambers view, (iii) an apical two chambers view, or (iv) a parasternal short-axis view.

Clause 9. The infusion system of any one of Clauses 1 through 8, wherein: the imaging probe is an ultrasound probe configured to generate an ultrasound image signal and wirelessly connect to the imaging device; and the imaging device is an ultrasound imaging device configured to receive the ultrasound image signal from the imaging probe and convert the ultrasound image signal into the image data.

Clause 10. A computer-implemented method for adjusting a patient care device based on image data, the method comprising: receiving an identifier of a fluid; determining based on the fluid identifier that the fluid is associated with an imaging-based infusion protocol; detecting whether an imaging device is connected to an imaging probe, wherein the imaging device is configured to receive an image signal from the imaging probe and convert the image signal into image data; responsive to detecting that the imaging device is connected to the imaging probe, operating an infusion device at a first operating speed during a first period of time, wherein the infusion device is configured to pump the fluid through an infusion line; receiving the image data from the imaging device; determining a second operating speed based on the image data; and operating the infusion device at the second operating speed during a second period of time subsequent to the first period of time.

Clause 11. The computer-implemented method of Clause 10, further comprising, responsive to detecting that the imaging device is connected to the imaging probe but prior to operating the infusion device at the first operating speed during the first period of time: prompting a user to image a patient with the imaging probe, wherein the patient is an intended recipient of the fluid to be pumped through the infusion line by the infusion device; receiving preliminary image data from the imaging device, wherein the preliminary image data is converted by the imaging device from a preliminary image signal received from the imaging probe; determining whether the preliminary image data satisfies a predetermined criterion; and delaying operating the infusion device at the first operating speed during the first period of time until after determining that the preliminary image data satisfies the predetermined criterion.

Clause 12. The computer-implemented method of Clause 11, wherein: the infusion line is fluidically coupled to the patient via a catheter; and determining whether the preliminary image data satisfies the predetermined criterion comprises determining whether the preliminary image data indicates that the catheter is properly inserted into the patient.

Clause 13. The computer-implemented method of any one of Clauses 10 through 12, further comprising: after operating the infusion device at the first operating speed during the first period of time but prior to receiving the image data from the imaging device, prompting a user to situate the imaging probe to image a particular area of a patient's body, wherein the patient is an intended recipient of the fluid to be pumped through the infusion line by the infusion device; responsive to receiving the image data but prior to determining the second operating speed based on the image data, confirming that the image data depicts the particular area of the patient's body; and delaying determining the second operating speed based on the image data until after determining that the image data depicts the particular area of the patient's body.

Clause 14. The computer-implemented method of Clause 13, further comprising: after operating the infusion device at the second operating speed during the second period of time but prior to receiving additional image data from the imaging device, prompting the user to situate the imaging probe to image another particular area of the patient's body; receiving the additional image data from the imaging device, wherein the additional image data is converted by the imaging device from an additional image signal received from the imaging probe; confirming that the additional image data depicts the other particular area of the patient's body; responsive to confirming that the additional data depicts the other particular area of the patient's body, determining a third operating speed based on the additional image data; and operating the infusion device at the third operating speed during a third period of time subsequent to the first and second periods of time.

Clause 15. The computer-implemented method of any one of Clauses 10 through 14, wherein determining the second operating speed based on the image data comprises: providing the image data to a machine-learning model trained using training image data and corresponding training operating speed adjustment data; and receiving the second operating speed from the machine-learning model.

Clause 16. The computer-implemented method of any one of Clauses 10 through 15, further comprising: after operating the infusion device at the first operating speed during the first period of time but prior to receiving the image data from the imaging device, prompt a user to obtain the image data by imaging a particular area of a patient's body with the imaging probe, wherein the patient is an intended recipient of the fluid to be pumped through the infusion line by the infusion device; and responsive to receiving the image data but prior to determining the second operating speed based on the image data, confirm that the image data depicts the particular area of the patient's body.

Clause 17. The computer-implemented method of Clause 16, further comprising: displaying, on a display screen, the image data in (i) a parasternal long axis view, (ii) an apical four chambers view, (iii) an apical two chambers view, or (iv) a parasternal short-axis view.

Clause 18. The infusion system of any one of Clauses 10 through 17, wherein: the imaging probe is an ultrasound probe configured to generate an ultrasound image signal and wirelessly connect to the imaging device; and the imaging device is an ultrasound imaging device configured to receive the ultrasound image signal from the imaging probe and convert the ultrasound image signal into the image data.

Clause 19. A non-transitory, computer-readable storage medium comprising instructions that when executed by a processor of an electronic device cause the processor to perform operations comprising: receiving an identifier of a fluid; determining based on the fluid identifier that the fluid is associated with an imaging-based infusion protocol; detecting whether an imaging device is connected to an imaging probe, wherein the imaging device is configured to receive an image signal from the imaging probe and convert the image signal into image data; responsive to detecting that the imaging device is connected to the imaging probe, operating an infusion device at a first operating speed during a first period of time, wherein the infusion device is configured to pump the fluid through an infusion line; receiving the image data from the imaging device; determining a second operating speed based on the image data; and operating the infusion device at the second operating speed during a second period of time subsequent to the first period of time.

Clause 20. The non-transitory, computer-readable medium of Clause 19, wherein the operations further comprise, responsive to detecting that the imaging device is connected to the imaging probe but prior to operating the infusion device at the first operating speed during the first period of time: prompting a user to image a patient with the imaging probe, wherein the patient is an intended recipient of the fluid to be pumped through the infusion line by the infusion device; receiving preliminary image data from the imaging device, wherein the preliminary image data is converted by the imaging device from a preliminary image signal received from the imaging probe; determining whether the preliminary image data satisfies a predetermined criterion; and delaying operating the infusion device at the first operating speed during the first period of time until after determining that the preliminary image data satisfies the predetermined criterion.

Further Consideration. The specific order or hierarchy of steps in the processes disclosed herein is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Those of skill in the art will appreciate that the various illustrative blocks, modules, elements, components, methods, and algorithms described herein may be implemented as electronic hardware, computer software, or a combination thereof. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Headings and subheadings, if any, are used for convenience only and do not limit the invention described herein.

The predicate words "configured to," "operable to," and "programmed to" do not imply any particular tangible or intangible modification of a subject, but rather are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as "implementations" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" and "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some implementations, include a signal utilized to transmit one or more representations of the information. While recited in the singular, it will be appreciated that a message may be composed, transmitted, stored, received, and so on in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine-learning assessment model, or combinations thereof.

In any implementation, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

What is claimed is:

1. An infusion system comprising:
an infusion device configured to pump a fluid through an infusion line;
an imaging device configured to receive an image signal from an imaging probe and convert the image signal into image data; and
a processor configured to:
receive an identifier of the fluid;
determine based on the fluid identifier that the fluid is associated with an imaging-based infusion protocol;
detect whether the imaging device is connected to the imaging probe;
responsive to detecting that the imaging device is connected to the imaging probe, operate the infusion device at a first operating speed during a first period of time;
receive the image data from the imaging device;
determine a second operating speed based on the image data; and
operate the infusion device at the second operating speed during a second period of time subsequent to the first period of time.

2. The infusion system of claim 1, wherein the processor is further configured to, responsive to detecting that the imaging device is connected to the imaging probe but prior to operating the infusion device at the first operating speed during the first period of time:
prompt a user to image a patient with the imaging probe, wherein the patient is an intended recipient of the fluid to be pumped through the infusion line by the infusion device;
receive preliminary image data from the imaging device, wherein the preliminary image data is converted by the imaging device from a preliminary image signal received from the imaging probe;
determine whether the preliminary image data satisfies a predetermined criterion; and
delay operating the infusion device at the first operating speed during the first period of time until after determining that the preliminary image data satisfies the predetermined criterion.

3. The infusion system of claim 2, wherein:
the infusion line is fluidically coupled to the patient via a catheter; and
determining whether the preliminary image data satisfies the predetermined criterion comprises determining whether the preliminary image data indicates that the catheter is properly inserted into the patient.

4. The infusion system of claim 1, wherein the processor is further configured to:
after operating the infusion device at the first operating speed during the first period of time but prior to receiving the image data from the imaging device, prompt a user to situate the imaging probe to image a particular area of a patient's body, wherein the patient is an intended recipient of the fluid to be pumped through the infusion line by the infusion device;

responsive to receiving the image data but prior to determining the second operating speed based on the image data, determine whether the image data depicts the particular area of the patient's body; and delay determining the second operating speed based on the image data until after determining that the image data depicts the particular area of the patient's body.

5. The infusion system of claim 4, wherein the processor is further configured to:

after operating the infusion device at the second operating speed during the second period of time but prior to receiving additional image data from the imaging device, prompt the user to situate the imaging probe to image another particular area of the patient's body;

receive the additional image data from the imaging device, wherein the additional image data is converted by the imaging device from an additional image signal received from the imaging probe;

confirm that the additional image data depicts the other particular area of the patient's body;

responsive to confirming that the additional data depicts the other particular area of the patient's body, determine a third operating speed based on the additional image data; and operate the infusion device at the third operating speed during a third period of time subsequent to the first and second periods of time.

6. The infusion system of claim 1, wherein determining the second operating speed based on the image data comprises:

providing the image data to a machine-learning model trained using training image data and corresponding training operating speed adjustment data; and receiving the second operating speed from the machine-learning model.

7. The infusion system of claim 1, wherein:

the processor is further configured to:

after operating the infusion device at the first operating speed during the first period of time but prior to receiving the image data from the imaging device, prompt a user situate the imaging device to obtain the image data by imaging a particular area of a patient's body, wherein the patient is an intended recipient of the fluid to be pumped through the infusion line by the infusion device; and responsive to receiving the image data but prior to determining the second operating speed based on the image data, confirm that the image data depicts the particular area of the patient's body.

8. The infusion system of claim 7, wherein the processor is further configured to:

display, on a display screen, the image data in (i) a parasternal long axis view, (ii) an apical four chambers view, (iii) an apical two chambers view, or (iv) a parasternal short-axis view.

9. The infusion system of claim 1, wherein:

the imaging probe is an ultrasound probe configured to generate an ultrasound image signal and wirelessly connect to the imaging device; and the imaging device is an ultrasound imaging device configured to receive the ultrasound image signal from the imaging probe and convert the ultrasound image signal into the image data.

10. A computer-implemented method for adjusting a patient care device based on image data, the method comprising:

receiving an identifier of a fluid;

determining based on the fluid identifier that the fluid is associated with an imaging-based infusion protocol;

detecting whether an imaging device is connected to an imaging probe, wherein the imaging device is configured to receive an image signal from the imaging probe and convert the image signal into image data;

responsive to detecting that the imaging device is connected to the imaging probe, operating an infusion device at a first operating speed during a first period of time, wherein the infusion device is configured to pump the fluid through an infusion line;

receiving the image data from the imaging device;

determining a second operating speed based on the image data; and operating the infusion device at the second operating speed during a second period of time subsequent to the first period of time.

11. The computer-implemented method of claim 10, further comprising, responsive to detecting that the imaging device is connected to the imaging probe but prior to operating the infusion device at the first operating speed during the first period of time:

prompting a user to image a patient with the imaging probe, wherein the patient is an intended recipient of the fluid to be pumped through the infusion line by the infusion device;

receiving preliminary image data from the imaging device, wherein the preliminary image data is converted by the imaging device from a preliminary image signal received from the imaging probe;

determining whether the preliminary image data satisfies a predetermined criterion; and delaying operating the infusion device at the first operating speed during the first period of time until after determining that the preliminary image data satisfies the predetermined criterion.

12. The computer-implemented method of claim 11, wherein:

the infusion line is fluidically coupled to the patient via a catheter; and determining whether the preliminary image data satisfies the predetermined criterion comprises determining whether the preliminary image data indicates that the catheter is properly inserted into the patient.

13. The computer-implemented method of claim 10, further comprising:

after operating the infusion device at the first operating speed during the first period of time but prior to receiving the image data from the imaging device, prompting a user to situate the imaging probe to image a particular area of a patient's body, wherein the patient is an intended recipient of the fluid to be pumped through the infusion line by the infusion device;

responsive to receiving the image data but prior to determining the second operating speed based on the image data, confirming that the image data depicts the particular area of the patient's body; and delaying determining the second operating speed based on the image data until after determining that the image data depicts the particular area of the patient's body.

14. The computer-implemented method of claim 13, further comprising:

after operating the infusion device at the second operating speed during the second period of time but prior to receiving additional image data from the imaging device, prompting the user to situate the imaging probe to image another particular area of the patient's body;

receiving the additional image data from the imaging device, wherein the additional image data is converted by the imaging device from an additional image signal received from the imaging probe;

confirming that the additional image data depicts the other particular area of the patient's body;

responsive to confirming that the additional data depicts the other particular area of the patient's body, determining a third operating speed based on the additional image data; and operating the infusion device at the third operating speed during a third period of time subsequent to the first and second periods of time.

15. The computer-implemented method of claim 10, wherein determining the second operating speed based on the image data comprises:

providing the image data to a machine-learning model trained using training image data and corresponding training operating speed adjustment data; and receiving the second operating speed from the machine-learning model.

16. The computer-implemented method of claim 10, further comprising:

after operating the infusion device at the first operating speed during the first period of time but prior to receiving the image data from the imaging device, prompt a user to obtain the image data by imaging a particular area of a patient's body with the imaging probe, wherein the patient is an intended recipient of the fluid to be pumped through the infusion line by the infusion device; and responsive to receiving the image data but prior to determining the second operating speed based on the image data, confirm that the image data depicts the particular area of the patient's body.

17. The computer-implemented method of claim 16, further comprising:

displaying, on a display screen, the image data in (i) a parasternal long axis view, (ii) an apical four chambers view, (iii) an apical two chambers view, or (iv) a parasternal short-axis view.

18. The computer-implemented method of claim 10, wherein:

the imaging probe is an ultrasound probe configured to generate an ultrasound image signal and wirelessly connect to the imaging device; and the imaging device is an ultrasound imaging device configured to receive the ultrasound image signal from the imaging probe and convert the ultrasound image signal into the image data.

19. A non-transitory, computer-readable storage medium comprising instructions that when executed by a processor of an electronic device cause the processor to perform operations comprising:

receiving an identifier of a fluid;

determining based on the fluid identifier that the fluid is associated with an imaging-based infusion protocol;

detecting whether an imaging device is connected to an imaging probe, wherein the imaging device is configured to receive an image signal from the imaging probe and convert the image signal into image data;

responsive to detecting that the imaging device is connected to the imaging probe, operating an infusion device at a first operating speed during a first period of time, wherein the infusion device is configured to pump the fluid through an infusion line;

receiving the image data from the imaging device;

determining a second operating speed based on the image data; and operating the infusion device at the second operating speed during a second period of time subsequent to the first period of time.

20. The non-transitory, computer-readable medium of claim 19, wherein the operations further comprise, responsive to detecting that the imaging device is connected to the imaging probe but prior to operating the infusion device at the first operating speed during the first period of time:

prompting a user to image a patient with the imaging probe, wherein the patient is an intended recipient of the fluid to be pumped through the infusion line by the infusion device;

receiving preliminary image data from the imaging device, wherein the preliminary image data is converted by the imaging device from a preliminary image signal received from the imaging probe;

determining whether the preliminary image data satisfies a predetermined criterion; and delaying operating the infusion device at the first operating speed during the first period of time until after determining that the preliminary image data satisfies the predetermined criterion.

* * * * *